United States Patent [19]

DeCarlo et al.

[11] Patent Number: 5,755,808
[45] Date of Patent: May 26, 1998

[54] CONNECTOR PLUG FOR MULTI-COMPONENT ORTHOPEDIC IMPLANT

[75] Inventors: A. Fred DeCarlo, Stamford, Conn.; Leda Hewka, Penthouse, N.Y.; Dario Vitali, Monroe, Conn.

[73] Assignee: Joint Medical Products, Corporation, Stamford, Conn.

[21] Appl. No.: 671,230

[22] Filed: Jun. 27, 1996

[51] Int. Cl.[6] ............................................. A61F 2/34
[52] U.S. Cl. ......................... 623/23; 623/22; 623/18
[58] Field of Search ......................... 623/18, 20, 22, 623/23, 19; 411/180; 606/74

[56] References Cited

U.S. PATENT DOCUMENTS

| | | | |
|---|---|---|---|
| 4,792,337 | 12/1988 | Muller | 623/22 |
| 4,938,773 | 7/1990 | Strand | 623/23 |
| 5,002,577 | 3/1991 | Bolesky et al. | 623/22 |
| 5,007,933 | 4/1991 | Sidebotham et al. | 623/18 |
| 5,019,103 | 5/1991 | Van Zile et al. | 623/20 |
| 5,092,897 | 3/1992 | Forte | 623/22 |
| 5,108,446 | 4/1992 | Wagner et al. | 623/22 |
| 5,133,763 | 7/1992 | Mullers | 623/22 |
| 5,137,535 | 8/1992 | Keller | 623/20 |
| 5,152,795 | 10/1992 | Sioshansi et al. | 623/22 |
| 5,201,882 | 4/1993 | Paxson | 623/23 |
| 5,282,864 | 2/1994 | Noiles et al. | 623/18 |
| 5,330,535 | 7/1994 | Moser et al. | 623/20 |
| 5,344,457 | 9/1994 | Pilliar et al. | 623/16 |
| 5,360,448 | 11/1994 | Thramann | 623/18 |
| 5,443,482 | 8/1995 | Stone et al. | 606/74 |
| 5,591,233 | 1/1997 | Kelman et al. | 623/22 |

FOREIGN PATENT DOCUMENTS

| | | | |
|---|---|---|---|
| 355035 | 2/1990 | European Pat. Off. | 17/58 |

*Primary Examiner*—John G. Weiss
*Assistant Examiner*—John M. Black

[57] ABSTRACT

A plug is provided for securing two components of an orthopedic implant where at least one of the components is formed of material softer than the material of the plug. In a preferred embodiment the components comprise concentric cups rotatable with respect to one another about an axis. The components are fixable using a plug to prevent rotation of the components with respect to each other. The invention is preferably used with an acetabular shell and liner of a hip implant wherein the shell is comprised of metal material and the liner is comprised of a polymer or other similar soft material. The plug has a serrated head and a distal lip or anchoring edge to provide securement at more than one location along the length of the plug. The plug is insertable into a common opening defined by aligned recesses or openings of the two components of the implant.

7 Claims, 5 Drawing Sheets

CONNECTOR PLUG FOR MULTI-COMPONENT ORTHOPEDIC IMPLANT

FIELD OF THE INVENTION

The present invention relates to a device for fastening two components of an orthopedic implant, preferably for connecting concentric cups of an implantable device.

BACKGROUND OF THE INVENTION

Many implantable artificial joints include a plurality of components that are movable with respect to each other for purposes of aligning and setting the joint in a patient. These components, once set in an optimal position, are then secured to each other or fixed so that the components do not move with respect to one another. For example, an asymmetric liner may be rotatable within and with respect to an outer cup to orient the asymmetric liner in an optimal position for implantation. The liner is then secured to the shell or cup using a pin. Typically, the pin will extend into a hole formed by common or aligned recesses or openings of the liner and cup. The pin extends from the liner through the hole exiting the shell as it abuts the acetabular or glenoid bone in the acetabulum or shoulder of the patient.

Such pins are usually comprised of a head portion and a clothespin type distal portion tapered to allow insertion into the hole and spring-loaded so that the clothespin end will tend to spread thus engaging the surfaces of the common opening of the liner and cup or shell. One potential disadvantage associated with this type of pin is that the pin must be long enough so that the spring force will engage and lock the component. Accordingly, the pin may extend into the acetabulum and in use, may loosen because of the forces of the acetabulum bone on the spring loaded distal portion.

It is therefore desirable to provide a means for attaching two implant components movable with respect to one another, to prevent loosening or movement of the components with respect to one another. It is also desirable to provide a means for fixing concentric cups of an implant system in a preferred aligned position with respect to one another.

SUMMARY OF THE INVENTION

Accordingly, the present invention provides a locking pin for locking a plurality of movably engaging components of a prosthetic implant into a selected optimal position. The plug is preferably used in an implant that comprises at least one component of a material softer than the material of the plug and a second component to be joined to the first component. Each of the two components comprises a recess, preferably a plurality of recesses, alignable with the recess or recesses of the other component to form one or more common conjoined openings.

The plug comprises a head having teeth or serrations, a body extending from the head having a proximal portion, a middle recess portion, and cylindrical conical distal end portion. The cylindrical conical distal end portion includes a lip and the proximal portion also includes a lip. Each of the lips are defined by the recessed middle portion. The lips are arranged to impinge surfaces of the softer material at separate opposing locations to hold the soft material component in a locked position with the other implant component. The dual lip feature of the plug permits more compact sizing of the plug and provides additional surface area contact between the plug and the conjoined elements.

The plug is preferably used with concentric cups of a socket type joint such as a hip or shoulder joint where an inner cup is rotatable with respect to outer cup about a common axis to optimally position the angular orientation of the inner cup. The implant comprises an outer metal shell and an inner cup made of a biocompatible polymer such as polyethylene. The plug is made of a metal such as a titanium alloy. The inner cup has two lugs extending into the hole formed by recesses in the shell and cup. The plug, when inserted, fits snugly within the hole and a lip and serrations on the head of the plug impinge on the lugs of the shell and prevent rotation of the liner within the shell.

In an alternative embodiment, the middle recessed portion may also include serrations for increasing the surface for resisting plug pull out force. These surfaces may be an alternative to or in addition to the lower lip of the plug.

DETAILED DESCRIPTION OF THE DRAWINGS

DETAILED DESCRIPTION OF THE INVENTION

Figure 1:
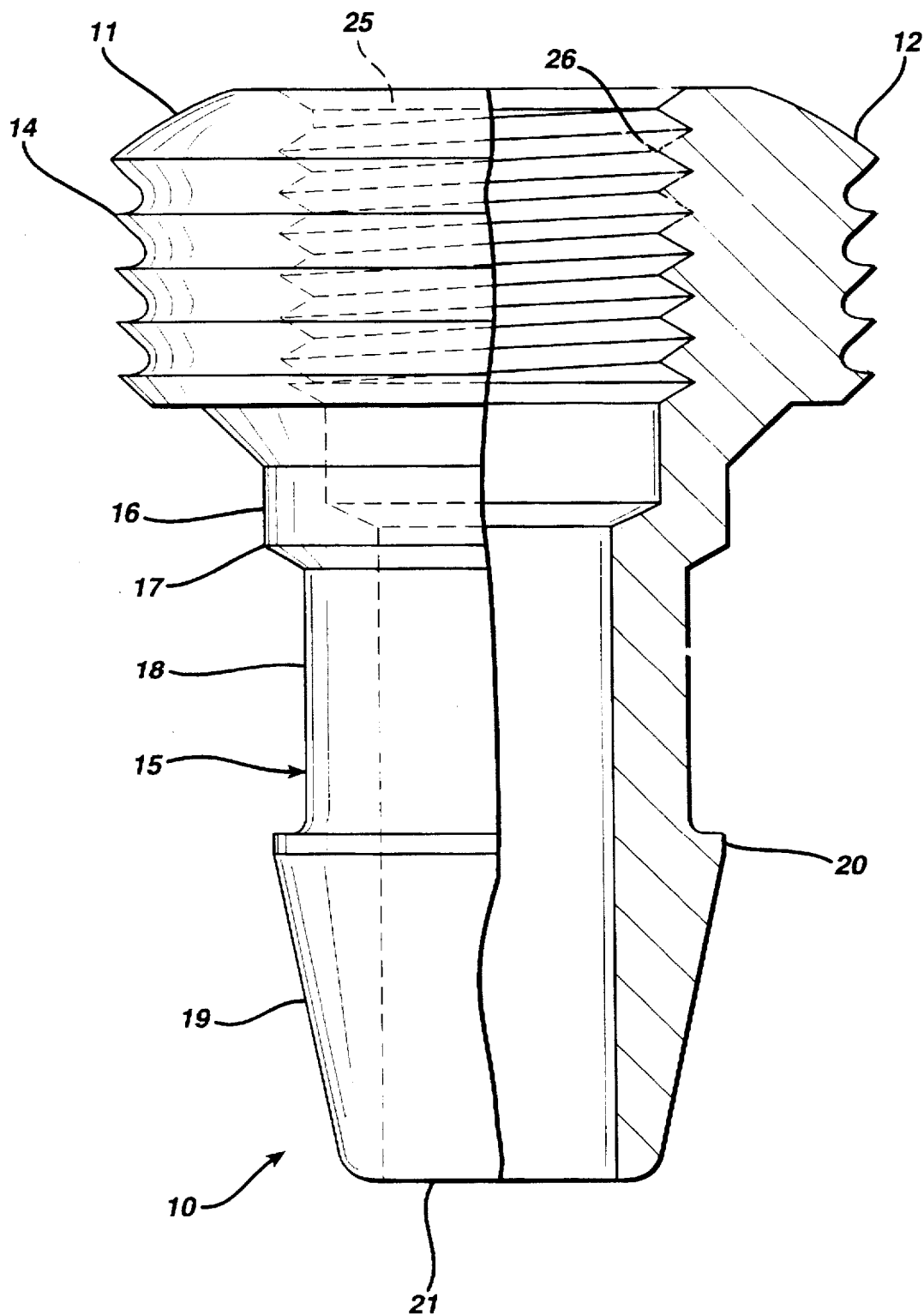
FIG. 1 illustrates a side partial cross view with phantom lines the plug of the present invention.
Figure 2:
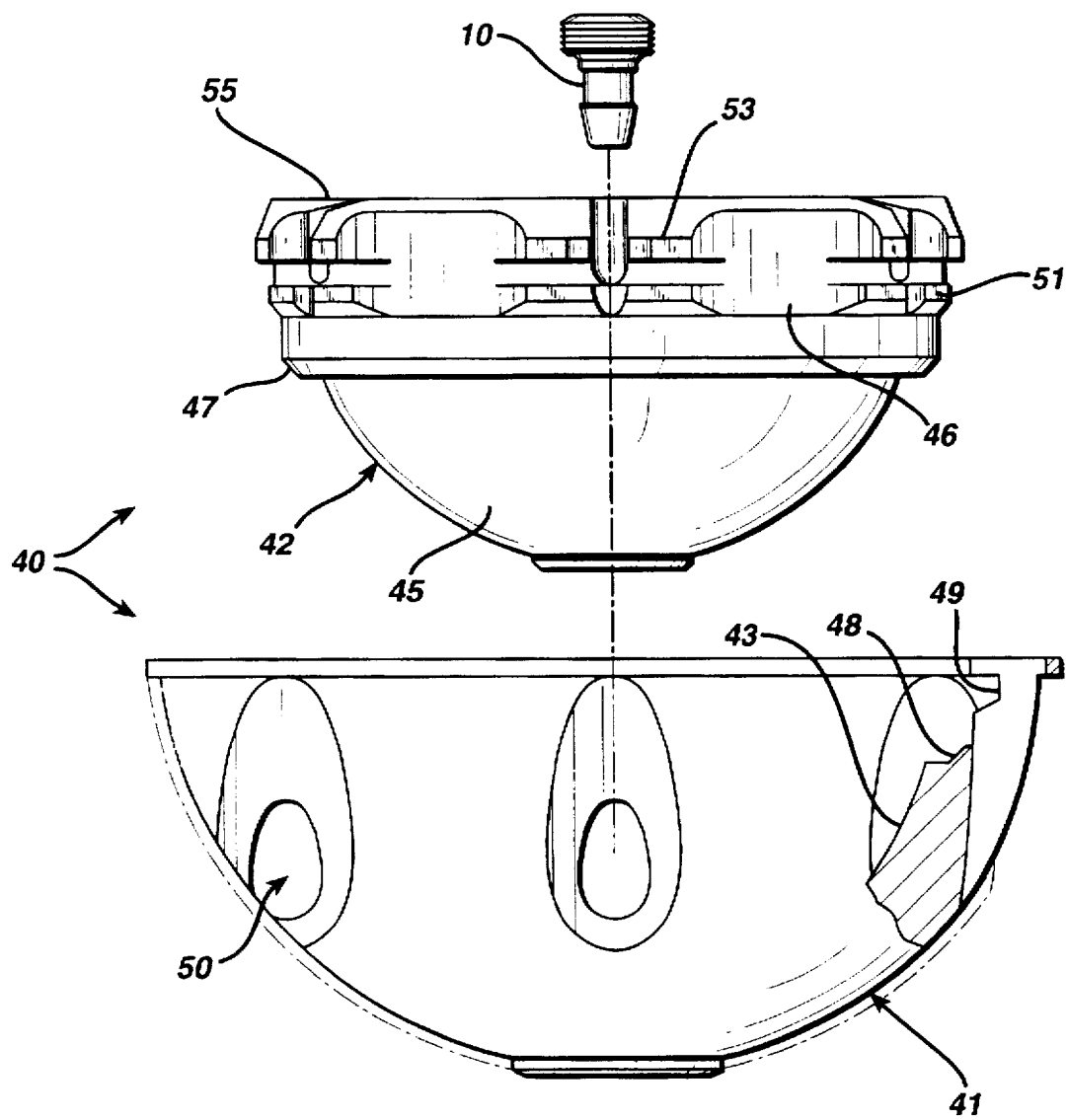
FIG. 2 illustrates a side view of the plug of the present invention in use with an acetabular shell (in partial cross section) and liner of a hip implant.
Figure 3:
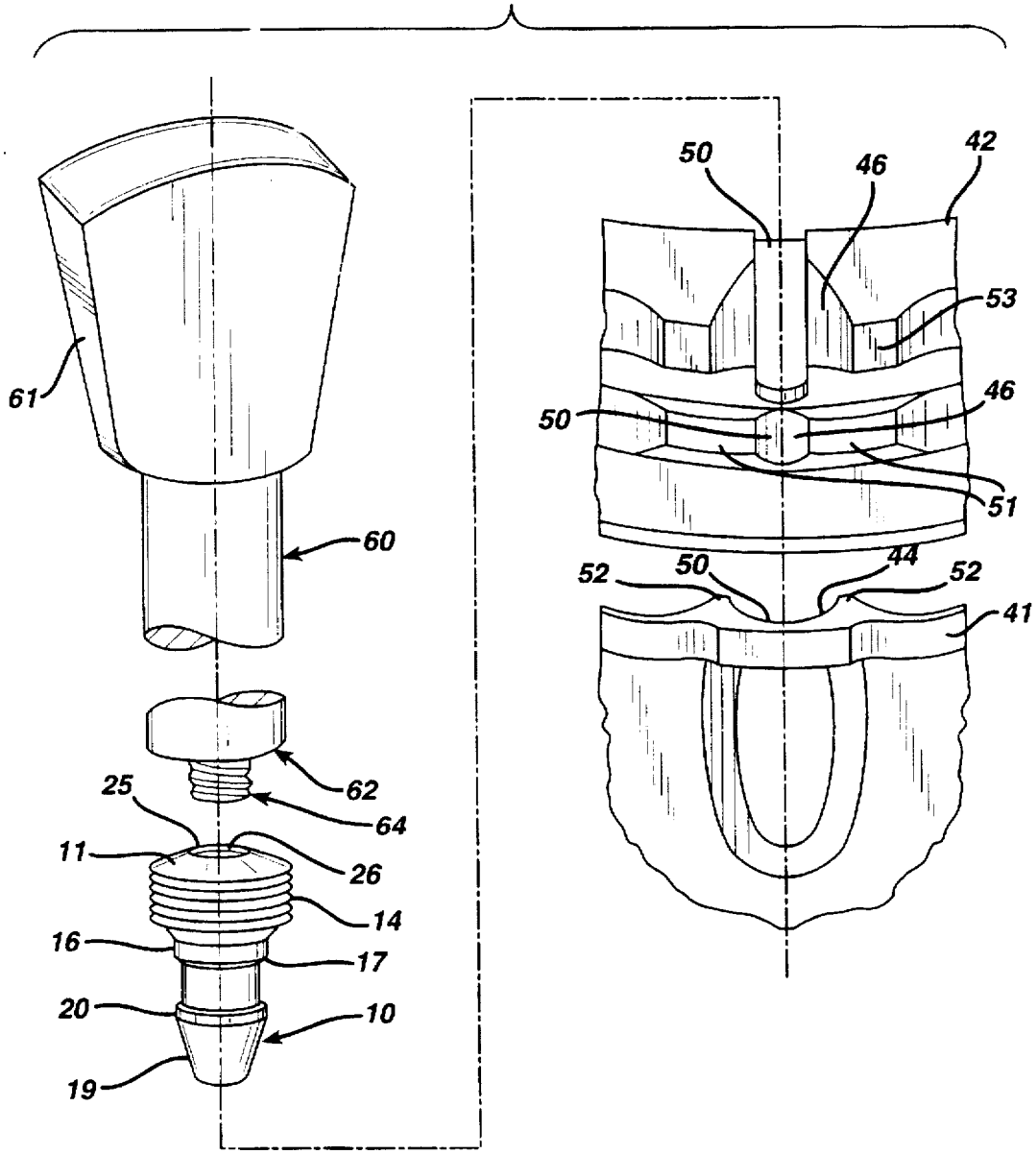
FIG. 3 illustrates an exploded view of the plug of the present invention in use with an acetabular shell and liner.
Figure 4:
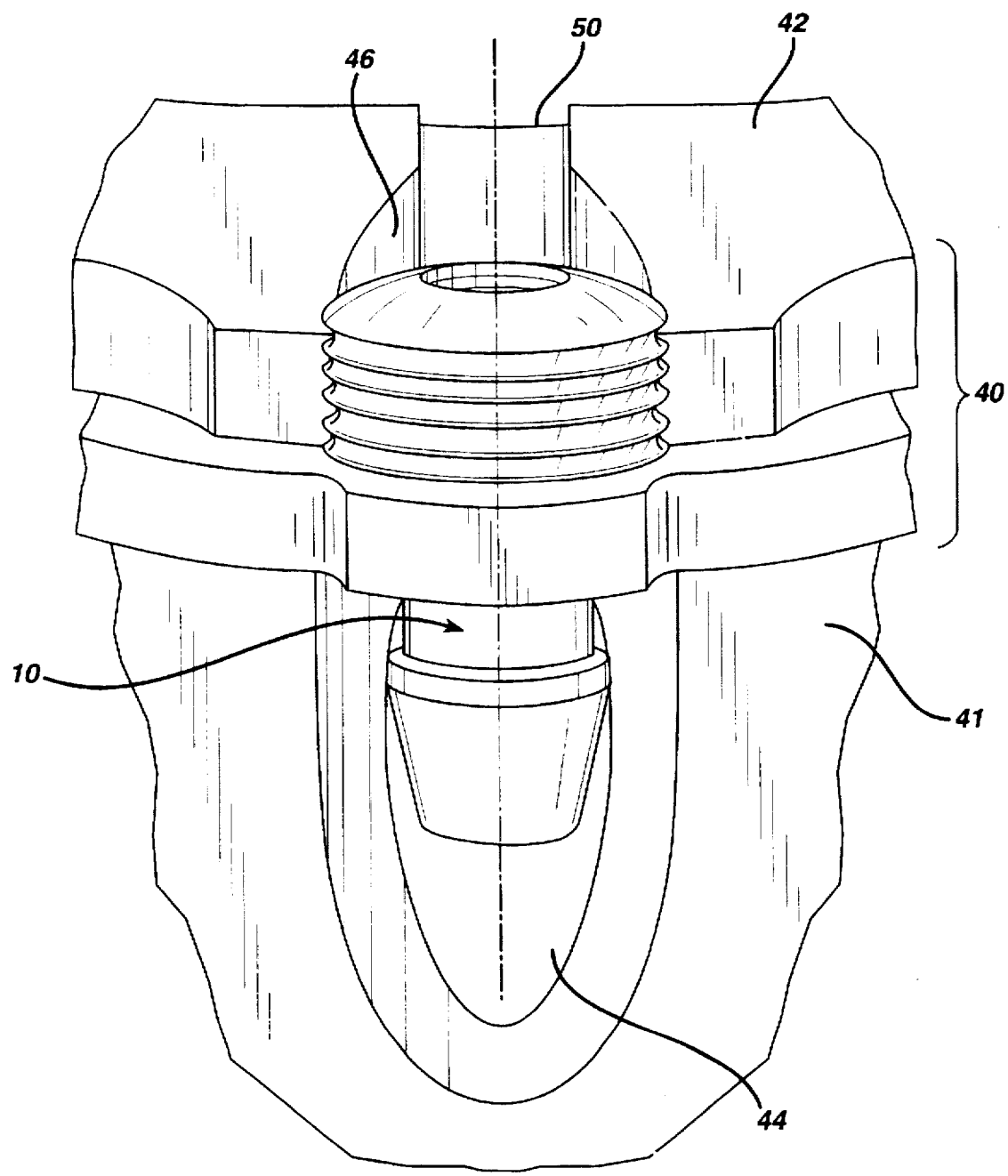
FIG. 4 illustrates the plug and cup of FIG. 3 with the plug inserted into the cup.

Referring now to FIGS. 1 through 4 there is illustrated an implant 40 and plug 10 of a preferred embodiment of the present invention. The plug 10 comprises a head 11 having serrations 14 on the outer circumference 12 of the head 11. The plug 10 further comprises a plug portion or body 15 comprising a proximal plug portion 16 having a lip 17 formed by a recessed portion 18 in the middle of the body 15. A conical portion 19 extends distally of the middle recessed portion 18. The conical portion 19 has a lip 20 formed where the middle recessed portion 18 joins the conical distal portion 19.

The conical distal portion 19 is tapered from the lip 20 to its distal point 21 to permit penetration through opening 50 defined by liner 42 and shell 41 of the implant 40. The plug 10 also has a blind opening 25 extending proximally to distally into the plug 10. The opening 25 includes a threaded inner portion 26 for attaching to an insertion instrument 60 with a threaded screw tip 64 for attaching into the threaded opening 25.

The implant 40 comprises an outer shell 41 and an inner liner 42. The shell 41 is preferably formed of a metal material such as titanium or cobalt chrome alloy and the liner 42 is preferably formed from a biocompatible polymer such as polyethylene. The liner 42 has an outer spherical surface 45 to be placed within shell 41 and articulate with an inner spherical surface 43 of the shell 41.

The shell 41 further comprises a series of recesses 44 located at various positions around the outer circumference of the shell 41. The liner 42 further also comprises a series of recesses 46 extending around the outer circumference of the liner 42. Recesses 44, 46 may be aligned to form holes 50 through which a plug 10 may be inserted.

The shell 41 also comprises a groove 48 for receiving a ridge 47 of the liner 42 to hold the liner 42 in position within the shell 42 and permit rotation of the liner 42 about a common axis of the shell 41 and liner 42. The outer shell 41 further comprises a second groove 49 above the first groove 48 for rotatably receiving lower lugs 51 in liner 42 located above the outer circumference of liner 42. The shell 41 also comprises protrusions 52 extending partially over groove 49 adjacent recesses 46 in the shell 41. The liner 42 is inserted into the shell 41 by a aligning the lower lugs 51 with the groove 49 where the groove 49 is uninterrupted by the protrusions 52. Once inserted, the lower lugs 51 may be rotated around the inner circumference of the shell 41 within groove 49. Lower lugs 51 are adjacent the recesses 46 in the liner 41 so that when the recesses 46 are aligned with the recesses 44, the protrusions 52 engage the lower lugs 51 preventing the liner 42 from being removed or lifted from the shell 41. The liner 42 further comprises upper lugs 53, also located adjacent openings or recesses 46. The upper lugs 53 rest on top of the inner circumference and protrusions 52 of the shell 41 when the liner 42 is inserted into the shell 41.

The plug 10 is insertable into a or hole 50 defined by recesses 44, 46. The threaded head 11 of the plug 10 is screwed into recesses 44, 46 using 25 with internal thread 26. The internal thread 26 attaches to the head 11 with an insertion instrument 60 having a handle 61 and a distal end 62 with mating threaded screw tip 64. The insertion instrument 60 is attached to the plug 10 and the conical point 19 of the plug 10 is inserted into the hole 50.

When the plug 10 is inserted, the distal lip 20 impinges on the lower lug 51 while the proximal lip 17 centers the plug 10 within the hole 50. The serrations 14 of the head 11 secure to or impinge the upper lug of 53 of the liner 41 thereby preventing loosening of the plug 10.

The outer diameter of conical point 19 and the proximal plug portion 16 at their greatest extent are roughly equal to the inner diameter of the hole 50, thereby permitting a snug fit of the plug 10 within the hole 50.

In use, the shell 41 is inserted into a bone cavity such as an acetabulum and the liner 42 is inserted into the shell 41. The lip 55 of the liner 41 has a varying angular orientation about the circumference of the liner 42. The liner 42 is oriented by rotating it within the shell 41 so that the lip 55 is located in an optimal position for implantation. The recesses 44 are aligned with the recesses 46 at the nearest adjacent location to this optimal lip 55 location. Plugs 10 are inserted into holes 50 formed by such alignment. Thus securing or locking the liner 42 within the shell 41 in its optimal location.

Figure 5:
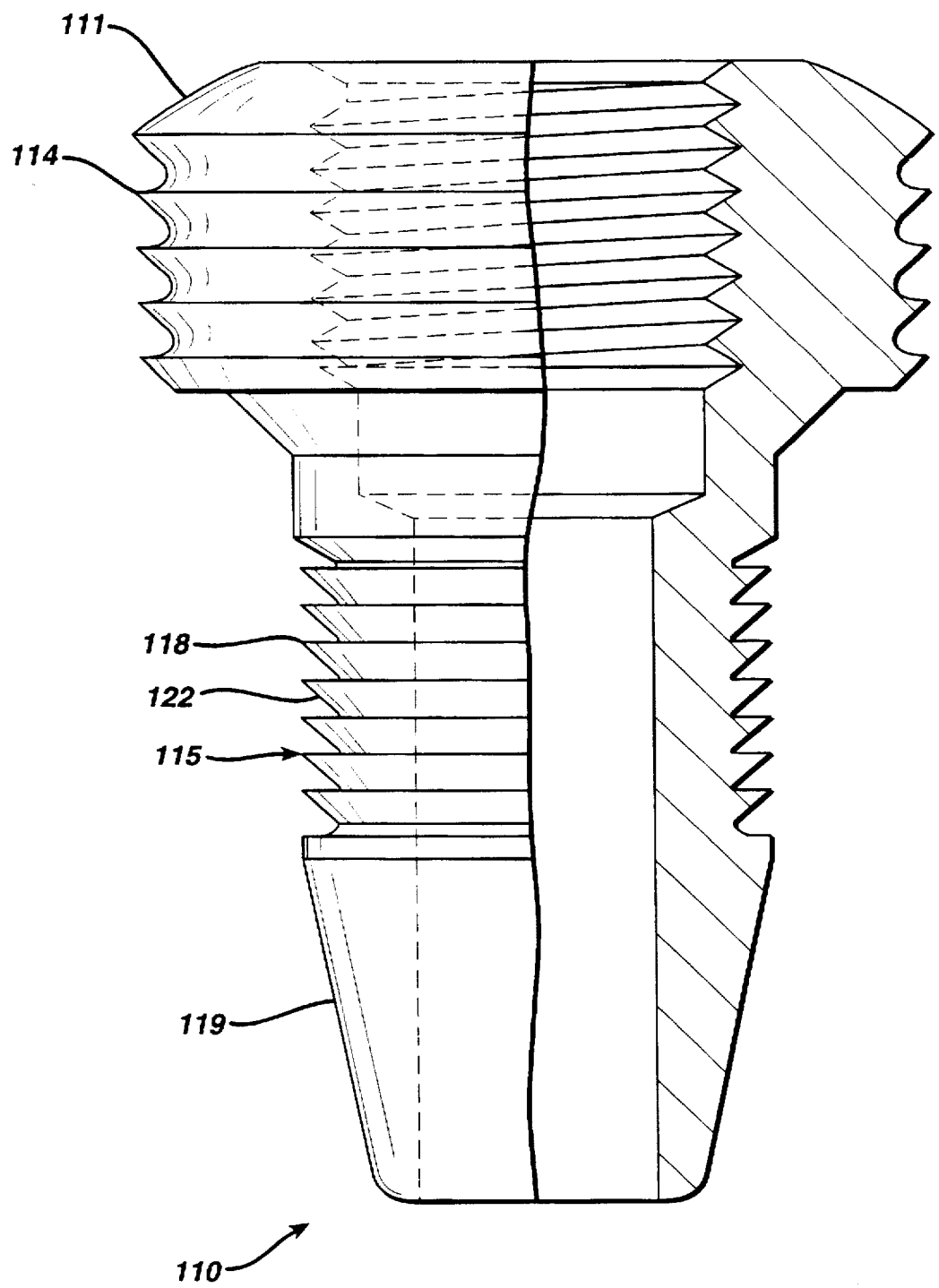
FIG. 5 illustrates an alternative embodiment of the plug.

Referring now to FIG. 5, an alternative embodiment is illustrated of a plug 110 having a head 111 with serrations 114 and a body 115 with a middle recessed portion 118 coupling a conical distal portion 119 to the head 111. The recessed portion 118 includes serrations 122 for engaging the liner 42 to the shell 41 of the implant.

Although this invention is described in connection with particular embodiments, numerous modifications may be made without departing from the scope of the invention claimed herein.

In the claims:

1. An orthopedic implant comprising a first component formed of a first material having a first hardness;
   a second component to be joined to said first component;
   a plug for locking said first and second components, said plug comprising:
   a head portion; and
   a body, said body comprising:
   a proximal portion coupled to said head;
   a conical cylindrical distal end portion; and
   a middle recessed portion coupling said proximal portion to said distal end portion;
   wherein said middle recessed portion defines a distal lip of said conical cylindrical distal end portion;
   wherein said first component comprises a recess and said second component comprises a recess, said recesses of said first and second components alignable to provide a common opening;
   wherein said body of said plug comprises an outer diameter and said common opening having a diameter substantially similar to the outer diameter of said body;
   wherein said first component comprises a first lug and second lug extending into said opening;
   wherein said head is engageable with said first lug and said plug distal lip engageable with said second lug to lock said first component with respect to said second component.

2. The orthopedic implant of claim 1 wherein said head further comprises an outer circumference having serrations thereon.

3. The orthopedic implant of claim 1 wherein said plug is comprised of a material having a hardness greater than said first hardness of said first component.

4. The orthopedic implant of claim 3 wherein said first component is comprised of a biocompatible polymer.

5. The orthopedic implant of claim 4 wherein said second component is comprised of a metal.

6. The orthopedic implant of claim 1 wherein said first component comprises a first cup having an outer convex spherical surface; and
   said second component comprises a second cup having an inner concave spherical surface, said first cup rotatable within said second cup so that said first spherical surface articulates with said second spherical surface;
   wherein said plug prevents rotation of said first cup with respect to said second cup when said plug is seated in said opening.

7. The orthopedic implant of claim 6 wherein said first component comprises a liner and said second cup comprises an acetabular shell.

* * * * *